US009267174B2

(12) United States Patent
Quake et al.

(10) Patent No.: US 9,267,174 B2
(45) Date of Patent: Feb. 23, 2016

(54) METHOD OF SIMULTANEOUSLY SCREENING FOR MULTIPLE GENOTYPES AND/OR MUTATIONS

(75) Inventors: Stephen R. Quake, Stanford, CA (US); Wei Gu, Stanford, CA (US); Hei-Mun Christina Fan, Stanford, CA (US)

(73) Assignee: Stanford University, Palo Alto, CA (US)

( * ) Notice: Subject to any disclaimer, the term of this patent is extended or adjusted under 35 U.S.C. 154(b) by 1079 days.

(21) Appl. No.: 13/282,249

(22) Filed: Oct. 26, 2011

(65) Prior Publication Data

US 2012/0108460 A1 May 3, 2012

Related U.S. Application Data

(60) Provisional application No. 61/406,809, filed on Oct. 26, 2010.

(51) Int. Cl.
*C12P 19/34* (2006.01)
*C12Q 1/68* (2006.01)
(52) U.S. Cl.
CPC ............ *C12Q 1/6881* (2013.01); *C12Q 1/6809* (2013.01); *C12Q 1/6883* (2013.01); *C12Q 2600/156* (2013.01)
(58) Field of Classification Search
USPC ................................................ 435/6.12, 91.2
See application file for complete search history.

(56) References Cited

U.S. PATENT DOCUMENTS

| 6,258,540 | B1 | 7/2001 | Lo et al. |
| 6,927,028 | B2 | 8/2005 | Dennis et al. |
| 7,332,277 | B2 | 2/2008 | Dhallan |
| 7,442,506 | B2 | 10/2008 | Dhallan |
| 7,709,194 | B2 | 5/2010 | Lo et al. |
| 2004/0137470 | A1 | 7/2004 | Dhallan |
| 2007/0202525 | A1 | 8/2007 | Quake et al. |
| 2009/0087847 | A1 | 4/2009 | Lo et al. |
| 2010/0216153 | A1 | 8/2010 | Lapidus et al. |
| 2010/0256013 | A1 | 10/2010 | Quake et al. |
| 2013/0116130 | A1* | 5/2013 | Fu et al. ............................ 506/4 |
| 2014/0186827 | A1* | 7/2014 | Pieprzyk et al. ............. 435/6.11 |

FOREIGN PATENT DOCUMENTS

WO 96/10648 A2 4/1996
WO 2007/147079 A2 12/2007

OTHER PUBLICATIONS

Y. M. Dennis Lo et al., "Plasma placental RNA allelic ratio permits noninvasive prenatal chromosomal aneuploidy detectoin," Nature Medicine, vol. 13, No. 2, XP55053181, pp. 218-223, Jan. 7, 2007.

(Continued)

*Primary Examiner* — Kenneth Horlick
(74) *Attorney, Agent, or Firm* — Rothwell, Figg, Ernst & Manbeck, P.C.

(57) ABSTRACT

The invention provides a non-invasive technique for the differential detection of multiple genotypes and/or mutations for a plurality of target genes in a biological sample containing genetic material from different genomic sources. Methods are conducted using multiplex amplification of a plurality of target sequences from the biological sample, and sequencing is used to detect and enumerate genetic mutations and chromosomal abnormalities at the single nucleotide level.

7 Claims, 3 Drawing Sheets

(56) References Cited

OTHER PUBLICATIONS

Y. M. Dennis Lo et al., "Prenatal diagnosis: progress through plasma nucleic acids," Nature Reviews Genetics, vol. 8, XP007905874, pp. 71-77, Jan. 1, 2007.

Extended European Search Report, issued in EP 11837024.6 on Apr. 3, 2014, 7 pages.

Fan et al., Non Invasive Diagnosis of Fetal Aneuploidy by Shotgun Sequencing DNA from Maternal Blood, Oct. 21, 2008, PNAS, vol. 105, No. 42.

Lun et al., Noninvasive prenatal diagnosis of monogenic diseases by digital size selection and relative mutation dosage on DNA in maternal plasma, Dec. 16, 2008, PNAS, vol. 105, No. 50.

Fan et al., Detection of Aneuploidy with Digital Polymerase Chain Reaction, Anal. Chem. 2007, 79, 7576-7579.

Tjoa et al., Trophoblastic Oxidative Stress and the Release of Cell-Free Feto-Placental DNA, Americal Journal of Pathology, vol. 169, No. 2, Aug. 2, 2006.

Pohl et al., Principle and applications of digital PCR, Expert Rev. Mol. Diagn. 4(1), 41-47 (2004).

International Search Report and Written Opinion for PCT/US11/57897 dated Feb. 21, 2012.

European Official Communication, issued in EP 11 837 024.6 on Feb. 19, 2015, 4 pages.

* cited by examiner

METHOD OF SIMULTANEOUSLY SCREENING FOR MULTIPLE GENOTYPES AND/OR MUTATIONS

RELATED APPLICATION

The present patent application claims the benefit of and priority to U.S. Provisional Patent Application Ser. No. 61/406,809 filed on Oct. 26, 2010, the entirety of which is herein incorporated by reference.

STATEMENT REGARDING FEDERALLY SPONSORED RESEARCH OR DEVELOPMENT

This invention was made with United States Government support under contract OD000251 awarded by the U.S. National Institute of Health. The Government has certain rights in this invention.

FIELD OF THE INVENTION

The present invention relates the field of quantitative nucleic acid analysis from a biological sample containing genetic material from different genomic sources. More specifically, the present invention provides a non-invasive technique for the differential detection of genotypes in a biological sample containing genetic material from different genomic sources.

BACKGROUND

Fetal DNA shed from the placenta is detectable in maternal blood at levels between 3% and 6% of total DNA. Thus, a number of PCR based fetal genetic screens have been described (e.g., gender, Rh, and thalassemia. However, traditional techniques are limited for at least two primary reasons: first, PCR assays trade sensitivity for specificity, often making it difficult to identify particular mutations, and second, aneuplodies, such as Down's Syndrome, cannot be detected by conventional PCR in a heterogeneous sample.

One way to avoid the problems of PCR-based assays is through large amounts of DNA using highly scalable techniques. Such digital analysis approaches involve the separation of extracted genomic material into discrete subsamples so that target sequence detection is binary (0, 1). For example, digital PCR allows amplification of single molecules, followed by quantitative analysis. Digital PCR typically requires limited dilution of a nucleic acid in a multi-well format followed by amplification of nucleic acids in the wells.

Digital PCR has been applied to fetal diagnostics in order to detect fetal mutations with specificity and sensitivity beyond that of conventional PCR. However, such methods are optimized for analyzing a single target in a biological sample, and moreover, the sample is consumed without interrogating the identity of other targets in the sample. Furthermore, digital PCR is limited to optical detection. Thus, multiplex analysis using digital PCR is not feasible, as it would be difficult to distinguish between optical signals for multiple targets in a given well. Additionally, conventional digital analysis does not allow for the detection of fetal single nucleotide polymorphisms (SNPs), which could be informative regarding a broad spectrum of diseases or conditions in the fetus. Thus, there is a need for improved methods for non-invasive, prenatal screening for multiple genotypes and/or mutations on many different targets genes at the single nucleotide level.

SUMMARY

The present invention provides methods for precise measurement of genomic instability in a plurality of different target regions in a biological sample containing genetic material from at least two different genomic sources. Methods of the invention involve the use of sequencing technology to digitally count a panel of selectively amplified targets contained in a heterogeneous biological sample. Methods of the invention provide for digital counting of target sequences, and afford more data via sequence reads than traditional methods of digital analysis, such as binary output digital PCR. As such, methods of the invention deliver a higher detection rate and improved clinical performance compared to conventional screening methods.

Methods of the invention are useful in any heterogeneous sample. Methods of the invention are especially useful for the detection of genetic disorders, and in particular for the detection of fetal genetic disorders. Methods provided herein are useful for detection of any genomic instability, such as a point mutation or an aneuploidy (e.g., trisomy, monosomy, duplication, deletion, addition, rearrangement, translocation, or inversion).

Methods of the invention are preferably performed on a biological sample containing a mixture of genetic material from at least two different genomic sources. A plurality of target sequences are amplified in the sample using primers flanking the region to be interrogated. Amplified target sequences are then directly sequenced and the amplicons are counted. Finally, the results are analyzed by comparison to a reference. For example, ratios of multiple amplified target sequences can be compared to detect aneuploidies; or sequence information can be compared to a reference sequence, or sequence obtained from another sample. Thus, a maternal sequence (e.g., obtained from a cheek swab) can be a reference or the reference can be from another individual or from a consensus sequence.

Unlike digital PCR, or other methods of digital analysis, methods of the invention are conducted without first diluting the biological sample or distributing the mixture of genetic material in the biological sample into discrete sub-samples. Methods of the invention are conducted, in part, by simultaneously amplifying a plurality of target sequences from heterogeneous biological sample containing a mixture of genetic material from different genomic sources. The amplified mixture of genetic material is then directly sequenced in order to digitally count the amplified strands (one strand per read).

Preferably, methods of the invention are conducted using single molecule sequencing technology, particularly sequencing-by-synthesis technologies. Sequencing technology to digitally count amplified strands of target sequences allows for the detection of fetal SNPs, as well as chromosomal abnormalities to detect a broad spectrum of fetal disorders.

Suitable sequencing-by-synthesis platforms that are useful with methods of the invention include, but are not limited to, True Single Molecule Sequencing (tSMS™) technology such as the HeliScope™ Sequencer offered by Helicos Inc. (Cambridge, Mass.), Single Molecule Real Time (SMRT™) technology, such as the PacBio RS system offered by Pacific Biosciences (California) and massively parallel sequencing technology, such as the HiSEQ2000 system offered by Illumina Inc. (San Diego, Calif.).

The simultaneous amplification of selected target sequences allows practitioners to customize prenatal screening tests for each parent. There is no limitation on the number of target sequences that can be analyzed using methods of the invention. The invention provides for the analysis of multiple genotypes and/or mutations for a plurality of target genes. Furthermore, an unlimited number of target sequences can be analyzed from a limited amount of biological sample without the need for enrichment. Although, one or more genomic populations of sequences may optionally be enriched for prior to amplifying and/or sequencing the target sequences. For example, anywhere from 2 to 100+ target sequences can be analyzed using methods of the invention.

A variety of genetic abnormalities may be differentially detected according to methods of the invention, including mutations, deletions, insertions, rearrangements, duplications, translocations and inversions in one or more target sequences. The invention is especially useful for the detection of SNPs, as well as aneuplodies (including whole chromosome duplications and deletions).

Examples of heterogeneous biological samples that contain a mixture of genetic material from different genomic sources include blood, a blood fraction (e.g., plasma), saliva, sputum, urine, semen, transvaginal fluid, sweat, breast milk, Breast fluid, cerebrospinal fluid, stool, a cell or a tissue biopsy. In general, the invention is useful to detect nucleic acid in a sample having nucleic acids from multiple genomic sources. In a certain embodiment, the heterogeneous biological sample is peripheral blood from a pregnant female, in particular the plasma derived from peripheral blood. The different genomic sources contributing the genetic material to the biological sample can be from a pregnant female and a fetus, a non-cancerous cell or a tissue and a cancerous cell or tissue, or from a donor tissue and a transplant recipient tissue. As such, methods of the invention are especially useful for non-invasive prenatal screening genetic mutations using cell-free fetal-DNA in maternal peripheral blood, and particularly useful for the detection of fetal SNPs and chromosomal abnormalities. However, the skilled artisan recognizes that methods of the invention are also useful to screen for a panel of target genes related to cancer using cell-free nucleic acids in blood, stool, sputum, urine, transvaginal fluid, breast nipple aspirate, cerebrospinal fluid, etc. Methods of the invention can also be used to screen for multiple genotypes and/or mutations for a variety of target genes in donor and transplant recipient tissue.

DETAILED DESCRIPTION

I. Overview

Figure 1:
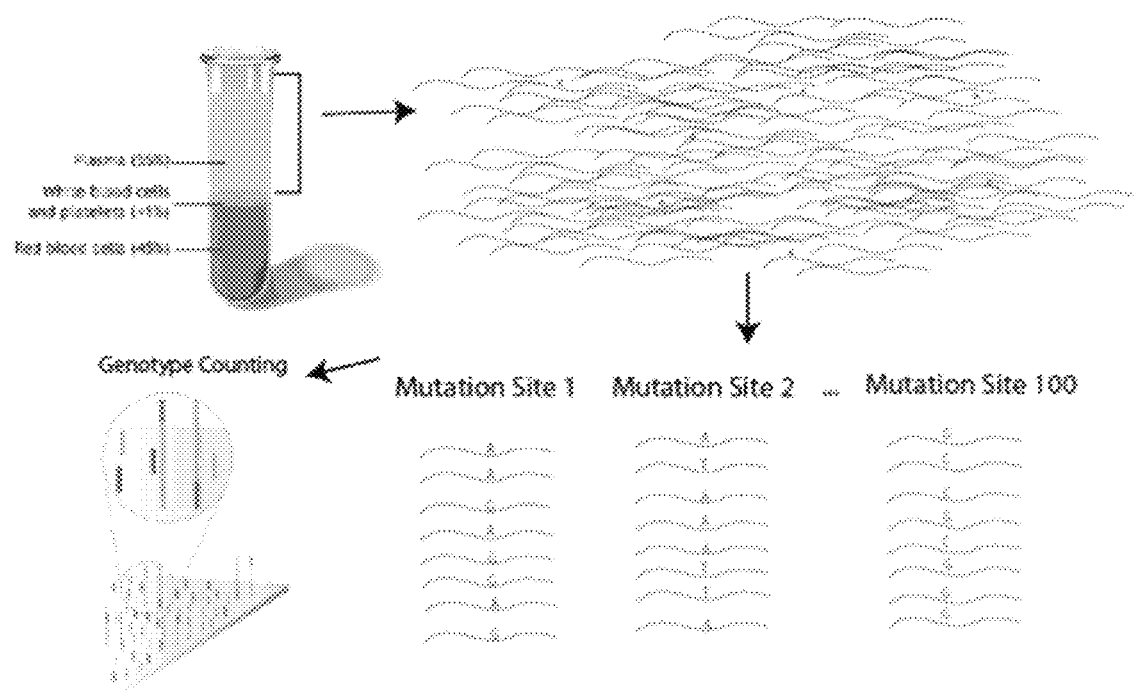
FIG. 1 is a schematic representation of fetal genotyping by sequencing.

Methods and materials described herein apply techniques for analyzing numerous target DNA sequences contained in a biological sample containing a mixture of genetic material from different genomic sources, and allow for the detection of differences between various target DNA sequences at the single nucleotide level.

Unlike other methods of digital analysis in which the DNA in the sample is isolated to a nominal single target molecule in a small reaction volume, methods of the present invention are conducted without diluting or distributing the genetic material in the sample. Methods of the invention allow for simultaneous screening of multiple genotypes and/or mutations for an unlimited number of target genes, and provide informative sequence information for each target gene at the single-nucleotide level, thus providing the capability for non-invasive, high throughput screening for a broad spectrum of diseases or conditions in a subject from a limited amount of biological sample.

In one particular embodiment, methods of the invention involve analysis of mixed fetal and maternal DNA in the maternal blood to identify a fetal mutation or genetic abnormality from the background of maternal DNA. Differential detection of target sequences is achieved, in part, by amplifying from the maternal blood a plurality of target sequences corresponding to multiple target genes, and using sequencing to differentially detect and count amplified strands. Methods and materials specific for analyzing nucleic acids in a biological sample containing mixed fetal and maternal DNA, as described herein, are merely one example of how methods of the invention can be applied and are not intended to limit the invention. Methods of the invention are also useful to screen for a panel of target genes related to cancer using cell-free nucleic acids in blood, stool, sputum, urine, transvaginal fluid, breast nipple aspirate, cerebrospinal fluid, etc. Methods of the invention can also be used to screen for multiple genotypes and/or mutations for a variety of target genes in donor and transplant recipient tissue.

Methods of the invention generally comprise the following steps:

A. Obtaining a biological sample containing genetic material from different genomic sources. The biological sample can be saliva, sputum, urine, semen, transvaginal fluid, cerebrospinal fluid, sweat, breast milk, breast fluid (e.g., breast nipple aspirate), stool, a cell or a tissue biopsy. In a particular embodiment, the biological sample is drawn blood and circulating DNA from different genomic sources is found in the blood or plasma, rather than in cells. The biological sample may optionally be enriched for DNA from one or more of the contributing genomic sources. For example, where the biological sample is blood or plasma containing a mixture of fetal and maternal DNA, the blood or plasma may be enriched by size fractionation to select for fetal DNA fragments, which tend to be less than about 300 bp. Alternatively, maternal DNA, which tends to be larger than about 500 bp, may be excluded. Another enrichment step may be to treat the blood sample with formaldehyde, as described in Dhallan et al. "Methods to Increase the Percentage of Free Fetal DNA Recovered From the Maternal Circulation", J. Am. Med. Soc. 291(9): 1114-1119 (2004).

B. Amplifying a plurality of target sequences from the biological sample containing a mixture of genetic material from different genomic sources, without diluting the genetic material or distributing the mixture of genetic material into discrete reaction samples, to obtain a sample containing an amplified mixture of genetic material from different genomic sources. Methods for simultaneously amplifying multiple target sequences in a single sample or reaction using more than one pair of primers, commonly referred to as multiplex amplification or multiplex PCR, have been described and are well known to one of ordinary skill in the art. Preferably, a plurality of primer pairs are designed to flank a plurality target sequences, as well as known mutation sites for the plurality of target sequences. Commercial kits for conducting multiplex available PCR are available from a variety of sources (e.g., QIAGEN Multiplex PCR Kit).

C. Sequencing the amplified mixture of genetic material. While any known sequencing method can be used to sequence the amplified mixture of genetic material in the amplified sample, single molecule (amplified or unamplified) sequencing methods are preferred. Such sequencing methods provide sequence information at the single nucleotide level and thus allow for the detection of mutations and other abnormalities that occur in one genotype in the biological sample, but not the other.

D. Counting the number of amplified sequences for each target sequence in the amplified sample. Counting is achieved via sequence reads (one read per amplified strand).

E. Conducting an analysis that compares the ratios of amplified target sequences to determine relative amounts of different target sequences in the biological sample.

A schematic of fetal genotyping by sequencing, according to methods of the invention, is shown in FIG. 1. After drawing blood from a pregnant female, plasma is immediately separated from cellular material presumably from the mother. The mixture of cell-free fetal and maternal DNA is then indiscriminately amplified at the same rate with flanking primers to each mutation site. Subsequent sequencing of the amplified strands results in digital counting of the target sites.

II. Description of Steps

A. Preparation of Biological Sample

The present method is directed to non-invasive testing. In a particular embodiment of the methods, the starting material is maternal blood. In order to obtain sufficient DNA for testing, it is preferred that 10-20 mL of blood be drawn, in order to obtain about at least 10,000 genome equivalents of total DNA. This sample size is based on an estimate of fetal DNA being present as roughly 25 genome equivalents/mL of maternal plasma in early pregnancy, and a fetal DNA concentration of about 3.4% of total plasma DNA. However, less blood may be drawn for a genetic screen in which less statistical significance is required, or in which the DNA sample is enriched for fetal DNA.

It should be noted that, while the present description refers throughout to fetal DNA, fetal RNA found in maternal blood may be analyzed as well. As described in Ng et al., "mRNA of placental origin is readily detectable in maternal plasma," Proc. Nat. Acad. Sci. 100(8): 4748-4753 (2003), hPL (human placental lactogen) and hCG (human chorionic gonadotropin) mRNA transcripts were detectable in maternal plasma, as analyzed using the respective real-time RT-PCR assays. In the present method, mRNA encoding genes expressed in the placenta and present on the chromosome of interest are used. For example, DSCR4 (Down syndrome critical region 4) is found on chromosome 21 and is mainly expressed in the placenta. Its mRNA sequence may be found at GenBank NM.sub.—005867. In this case, it is preferred to use RNase H minus (RNase H—) reverse transcriptases (RTs) to prepare cDNA for detection. RNase H—RTs are available from several manufacturers, with SuperScript™II (Invitrogen) being the most widely used. Reverse transcriptase PCR may be used as described below for chromosomal DNA.

i. Optional enrichment of DNA or RNA from Plasma

The maternal blood may be processed to enrich the fetal DNA concentration in the total DNA, as described in Li et al., supra. Briefly, circulatory DNA is extracted from 5- to 10-mL maternal plasma using commercial column technology (Roche High Pure Template DNA Purification Kit; Roche, Basel, Switzerland) in combination with a vacuum pump. After extraction, the DNA is separated by agarose gel (1%) electrophoresis (Invitrogen, Basel, Switzerland), and the gel fraction containing circulatory DNA with a size of approximately 300 bp is carefully excised. The DNA is extracted from this gel slice by using an extraction kit (QIAEX II Gel Extraction Kit; Qiagen, Basel, Switzerland) and eluted into a final volume of 40-.mu.L sterile 10-mM trishydrochloric acid, pH 8.0 (Roche).

DNA may be concentrated by known methods, including centrifugation and various enzyme inhibitors. The DNA is bound to a selective membrane (e.g., silica) to separate it from contaminants. The DNA is preferably enriched for fragments circulating in the plasma, which are less than 1000 base pairs ("bp") in length, generally less than 300 bp. This size selection is done on a DNA size separation medium, such as an electrophoretic gel or chromatography material. Such a material is described in Huber et al., "High-resolution liquid chromatography of DNA fragments on non-porous poly(styrene-divinylbenzene) particles," Nucleic Acids Res. 1993 Mar. 11; 21(5): 1061-1066, gel filtration chromatography, TSK gel, as described in Kato et al., "A New Packing for Separation of DNA Restriction Fragments by High Performance Liquid Chromatography," J. Biochem, 1984, Vol. 95, No. 1 83-86.

In addition, enrichment may be accomplished by suppression of certain alleles through the use of peptide nucleic acids (PNAs), which bind to their complementary target sequences, but do not amplify.

Plasma RNA extraction is described in Enders et al., "The Concentration of Circulating Corticotropin-releasing Hormone mRNA in Maternal Plasma Is Increased in Preeclampsia," Clinical Chemistry 49: 727-731, 2003. As described there, plasma harvested after centrifugation steps is mixed Trizol LS reagent (Invitrogen) and chloroform. The mixture is centrifuged, and the aqueous layer transferred to new tubes. Ethanol is added to the aqueous layer. The mixture is then applied to an RNeasy mini column (Qiagen) and processed according to the manufacturer's recommendations.

ii. Extraction of Fetal and/or Maternal Cells from Blood

United States Patent Application 20040137470 reports an enrichment procedure for fetal DNA. In this enrichment procedure, blood is collected into 9 ml EDTA Vacuette tubes (catalog number NC9897284), 0.225 ml of 10% neutral buffered solution containing formaldehyde (4% w/v) is added to each tube, and each tube gently is inverted. The tubes are stored at 4° C. until ready for processing.

Agents that impede cell lysis or stabilize cell membranes can be added to the tubes including but not limited to formaldehyde, and derivatives of formaldehyde, formalin, glutaraldehyde, and derivatives of glutaraldehyde, crosslinkers, primary amine reactive crosslinkers, sulfhydryl reactive crosslinkers, sulfhydryl addition or disulfide reduction, carbohydrate reactive crosslinkers, carboxyl reactive crosslinkers, photoreactive crosslinkers, cleavable crosslinkers, etc. Any concentration of agent that stabilizes cell membranes or impedes cell lysis can be added. In a preferred embodiment, the agent that stabilizes cell membranes or impedes cell lysis is added at a concentration that does not impede or hinder subsequent reactions.

Flow cytometry techniques can also be used to enrich fetal cells (Herzenberg et al., PNAS 76: 1453-1455 (1979); Bianchi et al., PNAS 87: 3279-3283 (1990); Bruch et al., Prenatal Diagnosis 11: 787-798 (1991)). U.S. Pat. No. 5,432,054 also describes a technique for separation of fetal nucleated red blood cells, using a tube having a wide top and a narrow, capillary bottom made of polyethylene. Centrifugation using a variable speed program results in a stacking of red blood cells in the capillary based on the density of the molecules. The density fraction containing low-density red blood cells, including fetal red blood cells, is recovered and then differentially hemolyzed to preferentially destroy maternal red blood cells. A density gradient in a hypertonic medium is used to separate red blood cells, now enriched in the fetal red blood cells from lymphocytes and ruptured maternal cells. The use of a hypertonic solution shrinks the red blood cells, which increases their density, and facilitates purification from the more dense lymphocytes. After the fetal cells have been isolated, fetal DNA can be purified using standard techniques in the art.

Further, an agent that stabilizes cell membranes may be added to the maternal blood to reduce maternal cell lysis including but not limited to aldehydes, urea formaldehyde, phenol formaldehyde, DMAE (dimethylaminoethanol), cholesterol, cholesterol derivatives, high concentrations of magnesium, vitamin E, and vitamin E derivatives, calcium, calcium gluconate, taurine, niacin, hydroxylamine derivatives, bimoclomol, sucrose, astaxanthin, glucose, amitriptyline, isomer A hopane tetral phenylacetate, isomer B hopane tetral phenylacetate, citicoline, inositol, vitamin B, vitamin B complex, cholesterol hemisuccinate, sorbitol, calcium, coenzyme Q, ubiquinone, vitamin K, vitamin K complex, menaquinone, zonegran, zinc, ginkgo biloba extract, diphenylhydantoin, perftoran, polyvinylpyrrolidone, phosphatidylserine, tegretol, PABA, disodium cromglycate, nedocromil sodium, phenyloin, zinc citrate, mexitil, dilantin, sodium hyaluronate, or polaxamer 188.

An example of a protocol for using this agent is as follows: The blood is stored at 4° C. until processing. The tubes are spun at 1000 rpm for ten minutes in a centrifuge with braking power set at zero. The tubes are spun a second time at 1000 rpm for ten minutes. The supernatant (the plasma) of each sample is transferred to a new tube and spun at 3000 rpm for ten minutes with the brake set at zero. The supernatant is transferred to a new tube and stored at −80° C. Approximately two milliliters of the "buffy coat," which contains maternal cells, is placed into a separate tube and stored at −80° C.

iii. Extraction of Free Fetal and/or Maternal DNA from Plasma

Genomic DNA may be isolated from the plasma using the QIAGEN Midi Kit for purification of DNA from blood cells, following the manufacturer's instructions (QIAmp DNA Blood Midi Kit, Catalog number 51183). DNA is eluted in 100 µl of distilled water. The QIAGEN Midi Kit also is used to isolate DNA from the maternal cells contained in the "buffy coat."

Finally, it is noted that, in certain embodiments, one may also use samples from saliva, sputum, urine, semen, transvaginal fluid, sweat, breast milk, breast fluid, cerebrospinal fluid, stool, a cell or a tissue biopsy, as previously described.

B. Amplification of Target Sequences

The present invention provides for the ability to simultaneously screen for multiple genotypes and/or mutations for a plurality of target genes in a limited amount of a biological sample using multiplex PCR techniques. Multiplex PCR is conducted using multiple primers within a single PCR mixture to produce amplicons of varying sizes that are specific to different DNA sequences. By targeting multiple genes at once, additional information may be gained from a single test run that otherwise would require several times the reagents and more time to perform. Annealing temperatures for each of the primer sets must be optimized to work correctly within a single reaction. Methods of conducting multiplex PCR reactions have been described and commercial kits for conducting multiplex PCR reactions are available for purchase (see e.g., QIAGEN Multiplex PCR Kit). Such commercial kits can be used in conjunction with specific primer pairs designed to detect target genes, gene mutations, and/or chromosomal abnormalities known to be involved in causing a disease or disorder in a subject, particularly a fetus. Preferably, a plurality of primer pairs are designed to flank a plurality target sequences, as well as known mutation sites for the plurality of target sequences.

For example, known alternations in one or more of the genes CFTR, Factor VIII, beta globin, hemachromatosis, G6PD, neurofibromatosis, GAPDH, beta amyloid, and pyruvate kinase have been linked to a variety diseases or disorders in a fetus. In addition, several fetal SNPs have been linked to premature rupture of membranes such as TNF-alpha (fetal TNF2 homozygous versus TNF1 homozygous mutation being 22% risk of being preterm rather than 3% risk), MMP8 (lowest risk haplotype 2.6%, highest risk haplotype 11.5%), SERPINH1 (2.8%->8.2% for the fetal alleles), MMPI (1.5%->3.4% for fetal carrier of mutation vs. homozygous for no mutation). Primers specific for one or more of these genes and/or known mutation thereof can be designed for use with methods of the invention. Primers specific for other genetic abnormalities, such as those involving a sequence which is deleted in a human chromosome, is moved in a translocation or inversion, or is duplicated in a chromosome duplication, may be designed by targeting genes known to be located on specific chromosomes, or chromosomal regions. As such, a variety of disease or disorders, including aneuploidies, may be detected by methods of the invention.

i. Primers

Primers can be prepared by a variety of methods including but not limited to cloning of appropriate sequences and direct chemical synthesis using methods well known in the art (Narang et al., Methods Enzymol. 68:90 (1979); Brown et al., Methods Enzymol. 68:109 (1979)). Primers can also be obtained from commercial sources such as Operon Technologies, Amersham Pharmacia Biotech, Sigma, and Life Technologies. The primers can have an identical melting temperature. The lengths of the primers can be extended or shortened at the 5' end or the 3' end to produce primers with desired melting temperatures. Also, the annealing position of each primer pair can be designed such that the sequence and, length of the primer pairs yield the desired melting temperature. The simplest equation for determining the melting temperature of primers smaller than 25 base pairs is the Wallace Rule (Td=2(A+T)+4(G+C)). Computer programs can also be used to design primers, including but not limited to Array Designer Software (Arrayit Inc.), Oligonucleotide Probe Sequence Design Software for Genetic Analysis (Olympus Optical Co.), NetPrimer, and DNAsis from Hitachi Software Engineering. The TM (melting or annealing temperature) of each primer is calculated using software programs such as Oligo Design, available from Invitrogen Corp.

The annealing temperature of the primers can be recalculated and increased after any cycle of amplification, including but not limited to cycle 1, 2, 3, 4, 5, cycles 6-10, cycles 10-15, cycles 15-20, cycles 20-25, cycles 25-30, cycles 30-35, or cycles 35-40. After the initial cycles of amplification, the 5' half of the primers is incorporated into the products from each loci of interest, thus the $T_M$ can be recalculated based on both the sequences of the 5' half and the 3' half of each primer.

A number of specific PCR primers are useful in the present process, such as those disclosed in technical literature of QIAGEN. That literature describes a protocol where DNA was purified from peripheral blood and amniocyte cultures using the QIAmp DNA Blood Mini Kit. For amplification of the amyloid gene on chromosome 21, (NCBI gene ID 473931, accession NC.sub.—006488) primer and probe sequences were: TABLE-US-00001 SEQ ID NO: 1: forward primer, 5'-GGG AGC TGG TAC AGA AAT GAC TTC-3';

reverse primer, SEQ ID NO: 10: 5'-TTG CTC ATT GCG CTG ACA A-3'; and probe, SEQ ID NO: 25'-(FAM) AGC CAT CCT TCC CGG GCC TAG G (TAMRA)-3'.

For amplification of GAPDH, (GenBank locus 12p13.31-p13.1) primers and probe were: forward primer, SEQ ID NO: 3,5'-CCC CAC ACA CAT GCA CTT ACC-3'; reverse primer, SEQ ID NO: 4,5'-CCT ACT CCC AGG GCT TTG ATT-3'; and probe, SEQ ID NO: 5,5'-(VIC) AAA GAG CTA GGA AGG ACA GGC AAC TTG GC (TAMRA)-3'. PCR was performed using the TaqMan system, with 2.mu.l of template DNA in each 25.mu.l reaction and final concentrations of 300 nmol/liter of each primer and 150 nmol/liter of each dual-labeled TaqMan probe. Cycling conditions were incubation at 50° C. for 2 minutes, then 95° C. for 10 minutes, followed by 40 cycles of 60° C., 1 minute and 95° C., 15 seconds.

Using the above exemplary protocol, the different ratio of the amyloid gene and the GAPDH gene in karyotypically normal and trisomy 21 samples was clearly distinguishable in the multiplex PCR assay, as reported in the QIAGEN product literature. Assays using a dilution series of the DNA template showed that the difference remained clear over a wide range of template concentrations and with starting concentrations of DNA as low as 10 mg/liter. Of course, in a maternal blood sample, the concentration of fetal DNA would be much lower.

ii. Polymerase

Any DNA polymerase that catalyzes primer extension can be used including but not limited to *E. coli* DNA polymerase, Klenow fragment of *E. coli* DNA polymerase 1, T7 DNA polymerase, T4 DNA polymerase, Taq polymerase, Pfu DNA polymerase, Vent DNA polymerase, bacteriophage 29, RED-Taq™. Genomic DNA polymerase, or sequenase. Preferably, a thermostable DNA polymerase is used. A "hot start" PCR can also be performed wherein the reaction is heated to 95° C. for two minutes prior to addition of the polymerase or the polymerase can be kept inactive until the first heating step in cycle 1. "Hot start" PCR can be used to minimize nonspecific amplification. Any number of PCR cycles can be used to amplify the DNA, including but not limited to 2, 5, 10, 15, 20, 25, 30, 35, 40, or 45 cycles. In a most preferred embodiment, the number of PCR cycles performed is such that equimolar amounts of each loci of interest are produced.

iii. Amplification Bias

Amplification bias (i.e., the preferential amplification of one target sequence over another) is a known phenomenon that occurs in multiplex PCR. The issue of amplification bias can be resolved by referencing one genotype relative to another to avoid amplification bias within one amplicon. However, when trying to determine the percentage of DNA in a sample containing genetic material from multiple genomic sources, comparisons between different amplicons are oftentimes necessary, and each amplicon is subject to amplification bias (e.g., the amounts of two different targets that are equal in amount pre-amplification, may be 2-fold different or more post-amplification).

Preliminary evidence has shown digital PCR results in less amplification bias for a single amplicon as compared to the Poisson sampling error. Methods of the invention account for amplification bias in a multiplex reaction by spiking the reaction with known or equal numbers of reference targets that can be used to detect relative or absolute amounts of the different sample targets. The reference target has a known sequence that varies by one or more base substitutions from that of the target gene. During amplification, if one sample target is amplified more than the other, the spiked reference can be used to normalize the values to derive relative and/or absolute copy numbers of the original sample targets by extrapolating from the reference spike (see Example 2 below). Sequencing can be used to obtain counts of sample and reference targets.

C. Direct Sequencing of Amplified Sample

Having amplified a plurality of target sequences from the undivided mixture of genetic material from multiple genomic sources, the presence of the DNA sequence and/or chromosome of interest must be detected. Detection of the amplified target sequences in the mixed biological sample may conveniently be carried out by direct sequencing.

As described Braslavsky et al., "Sequence information can be obtained from single DNA molecules", Proc. Nat. Acad. Sci. 100(7): 3960-3964 (2003), DNA polymerase may be employed to image sequence information in a single DNA template as its complementary strand is synthesized. The nucleotides are inserted sequentially; only the time resolution to discriminate successive incorporations is required. After each successful incorporation event, a fluorescent signal is measured and then nulled by photobleaching.

Briefly, this technique permits observations of single molecule fluorescence by a conventional microscope equipped with total internal reflection illumination, which reduces background fluorescence. The surface of a quartz slide is chemically treated to specifically anchor DNA templates while preventing nonspecific binding of free nucleotides, and a plastic flow cell is attached to the surface to exchange solutions. DNA template oligonucleotides are hybridized to a fluorescently labeled primer and bound to the surface via streptavidin and biotin with a surface density low enough to resolve single molecules. Polymerase and one fluorescently labeled nucleotide (C, G, A or T) are added. The polymerase catalyzes the sequence-specific incorporation of fluorescent nucleotides into nascent complementary strands on all the templates. After a wash step, which removes all free nucleotides, the incorporated nucleotides are imaged and their positions recorded. The fluorescent group is removed in a highly efficient cleavage process, leaving behind the incorporated nucleotide. The process continues through each of the other three bases. Multiple four-base cycles result in complementary strands greater than 25 bases in length synthesized on billions of templates—providing a greater than 25-base read from each of those individual templates. See products offered by Helicos, Inc. (Cambridge, Mass.), e.g., the HeliScope™ Single Molecule Sequencer. See Also products offered by Pacific Biosciences (California) e.g., the PacBio RS SMRT™ Sequencer.

Another methodology useful in the present invention platform is based on massively parallel sequencing of millions of fragments using attachment of randomly fragmented genomic DNA to a planar, optically transparent surface and solid phase amplification to create a high density sequencing flow cell with millions of clusters, each containing .about.1,000 copies of template per sq. cm. These templates are sequenced using four-color DNA sequencing-by-synthesis technology. See, products offered by Illumina, Inc. (San Diego, Calif.) e.g., the HiSEQ2000 system. Also, see US 2003/0022207 to Balasubramanian, et al., published Jan. 30, 2003, entitled "Arrayed polynucleotides and their use in genome analysis."

Only about 30 bp random sequence information are needed to identify a sequence as belonging to a specific human chromosome. Longer sequences can uniquely identify more particular targets. An algorithm for designing unique sequences is described in Yamada, et al. "PrimerStation: a highly specific multiplex genomic PCR primer design server for the human genome," Nucleic Acids Res., Jul. 1, 2006; 34 (Web Server issue): W665-W669, illustrative of software methods that can be used to identify a sequence in comparison to the known genome sequence. See, also Zhu et al., "Single molecule profiling of alternative pre-mRNA splicing," Science. 2003 Aug. 8; 301(5634):836-838, describing a single-molecule-based technology for studying mRNA.

D. Digital Counting

Detection of the plurality of amplified sequences in the mixed biological sample using sequencing analysis allows for digital counting of the number of amplified strands for each target sequence (one strand per read). Unlike previous methods of digital analysis, sequencing allows for the presence of multiple genotypes and/or mutations at the single nucleotide level to be detected and quantified for each of a plurality of targets sequences in a biological sample containing a mixture of genetic material from different genomic sources.

E. Analysis

After digitally counting the number of genotypes and/or mutations present in the sample for each of the plurality of target sequences, ratios of the genotypes and/or mutations for each of the target sequences can then be compared to determine the relative amounts of the target sequences and their various genotypes and/or mutated sequences in the biological sample. By counting the number of amplified target sequences from the mixture of genetic material in the biological sample, the over- or underrepresentation of any genetic abnormality in maternal plasma DNA contributed by a fetal genetic abnormality can be detected. For example, fetal genetic abnormalities including hereditary or non-hereditary mutations and chromosomal aberrations (e.g., translocation, inversion or deletion) can be detected. The enumerated target sequences can also be mapped to the chromosome of origin and the number of fragments per chromosome can be enumerated. By counting the number of sequence tags mapped to each chromosome, the over- or underrepresentation of any chromosome in maternal plasma DNA contributed by an aneuploid fetus can be detected.

It should be noted that methods of the invention do not require the differentiation of fetal versus maternal DNA, and with large enough sequence counts, methods of the invention can be applied to arbitrarily small fractions of fetal DNA. However, sequencing data from the amplified strands can be used to quantify the fetal fraction of DNA in maternal blood based on the maternal genetic contribution to the fetus. Given the limited fetal DNA fraction in a maternal blood sample, approximately 80-95% of the sequence counts for one allele are contributed by the mother. Thus, the sequencing counts for the amplified strands can be used to determine one or more loci where the mother is homozygous and to count the number of alleles different from that of the mother at the same locus. The presence of an allele other than the one contributed by the mother is an indication that the fetus is heterozygous at the same locus due to the paternal genetic contribution. The fetal fraction can be quantified based on the number of counts for each allele using the following equation:

Fetal fraction=2*(other allele count on locus where mother is homozygous)/(maternal homozygous allele count+other allele count on locus where mother is homozygous).

It should be noted that the fetal fraction for certain amplicons may be miscalculated if primer/DNA mismatches occur during the multiplex amplification step. This risk can be minimized by analyzing several different targets and quantifying the fetal fraction based on a consensus of counts from the different targets.

Utilities

Methods of the invention are useful for screening an individual at multiple loci of interest, such as tens, hundreds, or even thousands of loci of interest associated with a genetic trait or genetic disease by sequencing the loci of interest that are associated with the trait or disease state, especially those most frequently associated with such trait or condition. The invention is useful for analyzing a particular set of diseases including but not limited to heart disease, cancer, endocrine disorders, immune disorders, neurological disorders, musculoskeletal disorders, opthalmologic disorders, genetic abnormalities, trisomies, monosomies, transversions, translocations, skin disorders, and familial diseases.

Methods of the invention can also be used to confirm or identify the relationship of a DNA of unknown sequence to a DNA of known origin or sequence, for example, for use in, maternity or paternity testing, and the like.

Methods of the invention are especially useful for non-invasive prenatal screening for a panel of genetic mutations using fetal-DNA in maternal blood, and particularly useful for the detection of fetal SNPs and aneuplodies (including whole chromosomal duplications and deletions). However, the skilled artisan recognizes that methods of the invention can also be used to screen for a panel of target genes related to cancer using cell-free nucleic acids in blood, stool, sputum, urine, transvaginal fluid, breast nipple aspirate, cerebrospinal fluid, etc. Methods of the invention can also be used to screen for multiple genotypes and/or mutations for a variety of target genes in donor and transplant recipient tissue. A non-exhaustive listing of diseases and disorders that can be detected by methods of the invention are listed in Table 1 below.

TABLE 1

Achondroplasia
Adrenoleukodystrophy, X-Linked
Agammaglobulinemia, X-Linked
Alagille Syndrome
Alpha-Thalassemia X-Linked Mental Retardation Syndrome
Alzheimer Disease
Alzheimer Disease, Early-Onset Familial
Amyotrophic Lateral Sclerosis Overview
Androgen Insensitivity Syndrome
Angelman Syndrome
Ataxia Overview, Hereditary
Ataxia-Telangiectasia
Becker Muscular Dystrophy also The Dystrophinopathies)
Beckwith-Wiedemann Syndrome
Beta-Thalassemia
Biotinidase Deficiency
Branchiootorenal Syndrome
BRCA1 and BRCA2 Hereditary Breast/Ovarian Cancer
Breast Cancer
CADASIL
Canavan Disease
Cancer
Charcot-Marie-Tooth Hereditary Neuropathy
Charcot-Marie-Tooth Neuropathy Type 1
Charcot-Marie-Tooth Neuropathy Type 2
Charcot-Marie-Tooth Neuropathy Type 4
Charcot-Marie-Tooth Neuropathy Type X
Cockayne Syndrome
Colon Cancer
Contractural Arachnodactyly, Congenital
Craniosynostosis Syndromes (FGFR-Related)
Cystic Fibrosis
Cystinosis
Deafness and Hereditary Hearing Loss
DRPLA (Dentatorubral-Pallidoluysian Atrophy)
DiGeorge Syndrome (also 22q11 Deletion Syndrome)
Dilated Cardiomyopathy, X-Linked
Down Syndrome (Trisomy 21)
Duchenne Muscular Dystrophy (also The Dystrophinopathies)
Dystonia, Early-Onset Primary (DYT1)
Dystrophinopathies, The
Ehlers-Danlos Syndrome, Kyphoscoliotic Form
Ehlers-Danlos Syndrome, Vascular Type
Epidermolysis Bullosa Simplex

TABLE 1-continued

Exostoses, Hereditary Multiple
Facioscapulohumeral Muscular Dystrophy
Factor V Leiden Thrombophilia
Familial Adenomatous Polyposis (FAP)
Familial Mediterranean Fever
Fragile X Syndrome
Friedreich Ataxia
Frontotemporal Dementia with Parkinsonism-17
Galactosemia
Gaucher Disease
Hemochromatosis, Hereditary
Hemophilia A
Hemophilia B
Hemorrhagic Telangiectasia, Hereditary
Hearing Loss and Deafness, Nonsyndromic, DFNA (Connexin 26)
Hearing Loss and Deafness, Nonsyndromic, DFNB 1 (Connexin 26)
Hereditary Spastic Paraplegia
Hermansky-Pudlak Syndrome
Hexosaminidase A Deficiency (also Tay-Sachs)
Huntington Disease
Hypochondroplasia
Ichthyosis, Congenital, Autosomal Recessive
Incontinentia Pigmenti
Kennedy Disease (also Spinal and Bulbar Muscular Atrophy)
Krabbe Disease
Leber Hereditary Optic Neuropathy
Lesch-Nyhan Syndrome Leukemias
Li-Fraumeni Syndrome
Limb-Girdle Muscular Dystrophy
Lipoprotein Lipase Deficiency, Familial
Lissencephaly
Marfan Syndrome
MELAS (Mitochondrial Encephalomyopathy, Lactic Acidosis, and Stroke-Like Episodes)
Monosomies
Multiple Endocrine Neoplasia Type 2
Multiple Exostoses, Hereditary Muscular Dystrophy, Congenital
Myotonic Dystrophy
Nephrogenic Diabetes Insipidus
Neurofibromatosis 1
Neurofibromatosis 2
Neuropathy with Liability to Pressure Palsies, Hereditary
Niemann-Pick Disease Type C
Nijmegen Breakage Syndrome Norrie Disease
Oculocutaneous Albinism Type 1
Oculopharyngeal Muscular Dystrophy
Ovarian Cancer
Pallister-Hall Syndrome
Parkin Type of Juvenile Parkinson Disease
Pelizaeus-Merzbacher Disease
Pendred Syndrome
Peutz-Jeghers Syndrome Phenylalanine Hydroxylase Deficiency
Prader-Willi Syndrome
PROP 1-Related Combined Pituitary Hormone Deficiency (CPHD)
Prostate Cancer
Retinitis Pigmentosa
Retinoblastoma
Rothmund-Thomson Syndrome
Smith-Lemli-Opitz Syndrome
Spastic Paraplegia, Hereditary
Spinal and Bulbar Muscular Atrophy (also Kennedy Disease)
Spinal Muscular Atrophy
Spinocerebellar Ataxia Type 1
Spinocerebellar Ataxia Type 2
Spinocerebellar Ataxia Type 3
Spinocerebellar Ataxia Type 6
Spinocerebellar Ataxia Type 7
Stickler Syndrome (Hereditary Arthroophthalmopathy)
Tay-Sachs (also GM2 Gangliosidoses)
Trisomies
Tuberous Sclerosis Complex
Usher Syndrome Type I
Usher Syndrome Type II

TABLE 1-continued

Velocardiofacial Syndrome (also 22q11 Deletion Syndrome)
Von Hippel-Lindau Syndrome
Williams Syndrome
Wilson Disease
X-Linked Adrenoleukodystrophy
X-Linked Agammaglobulinemia
X-Linked Dilated Cardiomyopathy (also The Dystrophinopathies)
X-Linked Hypotonic Facies Mental Retardation Syndrome

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered iii all respects illustrative rather than limiting on the invention described herein. Scope of the invention is thus indicated by the appended claims rather than by the foregoing description, and all changes which come within the meaning and range of equivalency of the claims are therefore intended to be embraced therein.

EXAMPLES

Example 1

Detection of Fetal Genetic Abnormalities in Maternal Blood

The amount of fetal DNA in maternal blood varies widely and increases over the course of pregnancy. In early pregnancy, the level of fetal DNA present in maternal blood may not be sufficient to resolve differences in proportions of maternal and fetal DNA. The difference in proportions of maternal and fetal DNA in maternal blood can be estimated. Calculations based on a Poisson distribution of finite target allele counts are as follows:

DEFINITIONS $$\varepsilon = \frac{\text{fetal\_DNA}}{\text{total\_DNA}}, N_T = \text{\# total alleles} = N_M + N_W,$$

$$N_M = \text{\# mutant alleles}, N_W = \text{\# wildtype alleles}$$

Figure 2:
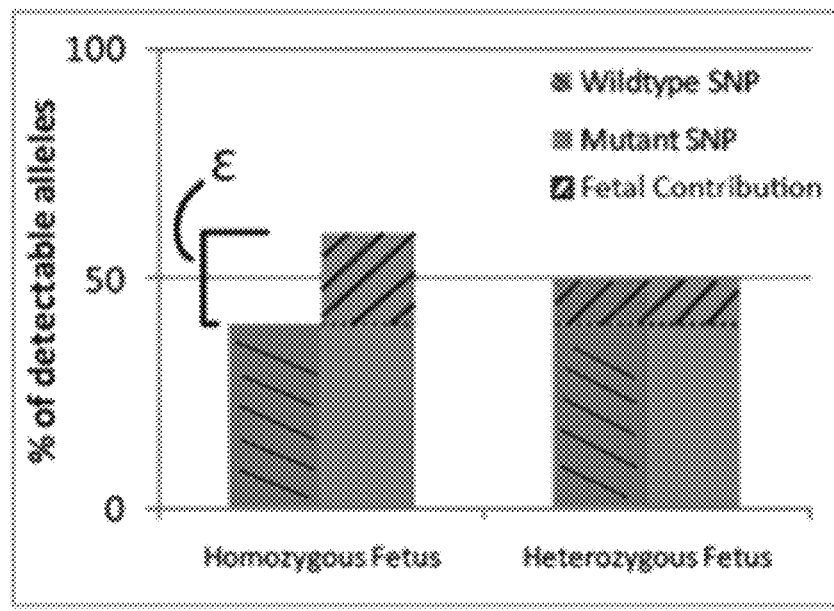
FIG. 2 is a graph depicting theoretical averages assuming a maternal carrier for a mutation and matchup between the clinically relevant fetal states. $\epsilon$ is the fraction of alleles that are detectable which is the same as the difference between the wildtype and mutant allele in the homozygous fetus.

The equation above is exemplified in FIG. 2, which shows theoretical fetal counts averages assuming a maternal carrier for a mutation. $\varepsilon$ is the fraction of alleles that are detectable which is the same as the difference between the wildtype and mutant allele in the homozygous fetus.

Homozygous case:

$$N_M - N_W = \varepsilon * N_T$$

Heterozygous case:

$$N_M - N_W = 0$$

Homozygous case:

$$\sigma \text{ of } N_M = \sqrt{0.5 * N_T + 0.5 * \epsilon}$$

$$\sigma \text{ of } N_W = \sqrt{0.5 * N_T - 0.5 * \epsilon}$$

$$\sigma \text{ of } N_M - N_W = \sqrt{\left(\sqrt{0.5 * N_T + 0.5 * \epsilon}\right)^2 + \left(\sqrt{0.5 * N_T - 0.5 * \epsilon}\right)^2} = \sqrt{N_T}$$

Heterozygous case:

$$\sigma \text{ of } N_M \text{ or } N_W = \sqrt{0.5 * N_T}$$

$$\sigma \text{ of } N_M - N_W = \sqrt{\left(\sqrt{0.5 * N_T}\right)^2 + \left(\sqrt{0.5 * N_T}\right)^2} = \sqrt{N_T}$$

(same as the homozygous case)
standard deviations achievable at halfway cutoff between 0 and $\epsilon * N_T$ ($Z = 0.5 * \epsilon * N_T$)=

$$\frac{Z}{\sigma} = \frac{0.5 * (N_M - N_W)}{\sqrt{N_T}} = \frac{0.5 * (\epsilon * N_T)}{\sqrt{N_T}} \quad \text{(Equation 1)}$$

Figure 3:
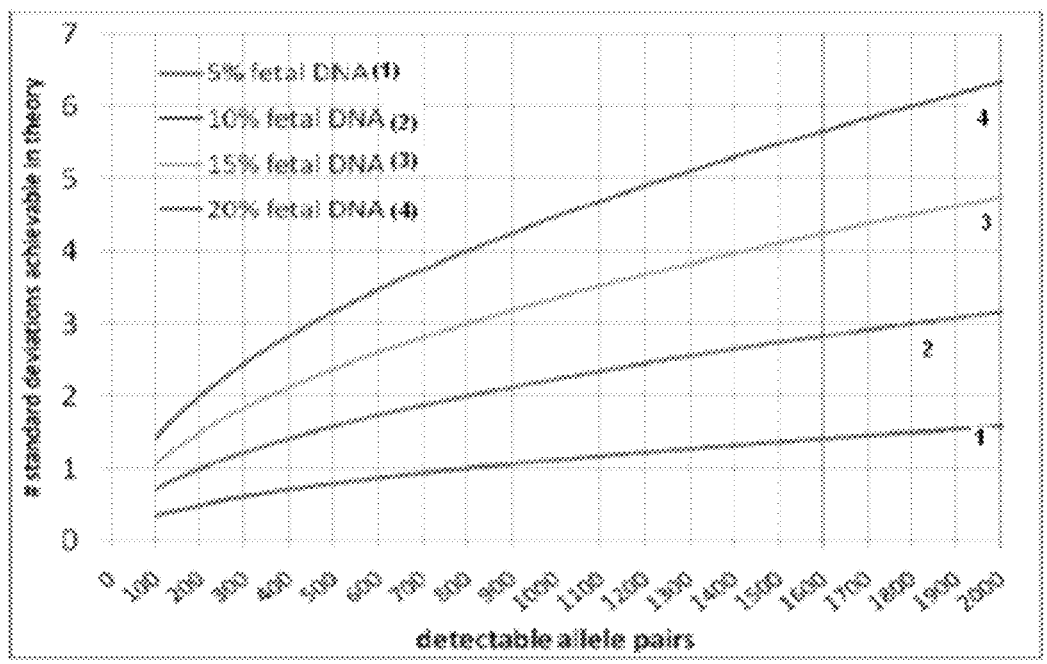
FIG. 3 is a graph depicting the number of theoretically based standard deviations for a given condition.

The graph shown in FIG. 3 displays the outcome of Equation 1 at different detectable allele pair counts and different percentages of DNA. Actual targets will have more genetic content than detectable alleles because mutations located at the edge of a DNA fragment will not amplify. For example, an 85 bp amplicon will only amplify approximately half of the strands contained in the targeted allele, given that the allele location is evenly distributed on the stereotypical 170 bp fetal strand.

There is a range of 57-761 cell equivalents per mL plasma. Assuming that half the strands in the sample are usable (due to the short length of cell-free fragments and aligning that with a full amplicon) if a pregnant female is on the low end that range, then approximately 120 mL of plasma will be necessary to obtain 3400 counts.

Example 2

Avoiding Amplification Bias while Screening for a Panel of Genetic Mutations

Amplification bias is a known problem in multiplex PCR. Amplification bias can be resolved by referencing one genotype relative to another within one amplicon. However, to obtain the fetal fraction of DNA in a sample, comparisons between different amplicons are necessary, and each amplicon will be subject to amplification bias (e.g., the amounts of two different targets that are equal in amount pre-amplification, may be 2-fold different or more post-amplification).

Preliminary evidence has shown digital PCR results in less amplification bias for a single amplicon as compared to the Poisson sampling error. If one were to spike a multiplex PCR reaction with known or equal numbers of reference targets with known sequences, the reference targets could then be used to detect relative or absolute amounts of the different sample targets.

Figure 4:
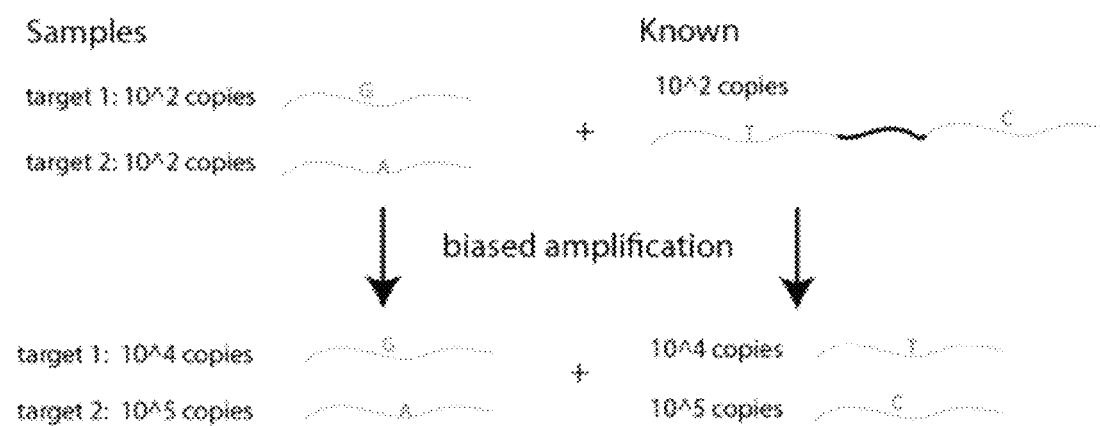
FIG. 4 is a schematic depicting a method for correcting for amplification bias using when using digital sequencing technology.

For example, if one were to conduct a multiplex PCR reaction starting with 100 molecules of two different targets, each having its own primer set, our method involves spiking into the multiplex PCR reaction known or equal amounts of two reference targets that vary from the actual targets by only one or more base substitutions (FIG. 4). During amplification, if one target is amplified more than the other, the spiked reference can be used to normalize the two values to derive relative and/or absolute copy numbers of the original sample targets by extrapolating from the reference spike. To arrive at the actual ratio, one takes the digital counts for sample Target1/Target2 and multiply by reference Target2/Target1, to obtain close to 1:1, the actual starting ratio.

Example 3

Protocol for Prenatal Screening for a Genetic Disease

1. Perform carrier screen to obtain SNPs that are homozygous and different for the mother and father.
2. If both parents are carriers, or mother is a carrier and father is unknown, then proceed with prenatal diagnostics in accordance with the methods of the invention. Optionally, SNPs that are different between mother and fetus are used to estimate the percentage of fetal DNA in the sample. If screening occurs during earlier stages of pregnancy, a larger biological sample size is preferable (e.g., 40 mL blood to yield 20 mL plasma).
3. Optionally, the fetal DNA in the biological sample can be enriched by treating the blood sample with formaldehyde (see Dhallan et al., J. Am. Med. Soc. 291(9): 1114-1119 (2004)).
4. Amplify the target gene known or suspected to be involved in a fetal genetic mutation and/or chromosomal abnormalities, as described above. Preferably, DNA is amplified with the smallest amplicon size to avoid amplification bias. The primer set is designed so as not to be dependent on an allele. Two rounds of multiplex amplification may be necessary to dilute out the rest of the genome(s).
5. Perform sequencing runs to detect and digitally count amplified strands.

Example 4

Protocol for Prenatal Screening for One or More Diseases Using a Customized Panel 1. Perform carrier test on mother, checking for SNP sites that have known polymorphisms.
2. Knowing the carrier status of the mother, there will be on average approximately 5 sever recessive diseases that the fetus can inherit. A panel of the most common mutations is assembled based on those possibilities to detect a homozygous recessive fetus or an affected compound heterozygote. A panel of SNPs can be added to the screen where the fetus may have different allele at a site where the mother is homozygous. Determining those sites will allow for proper quantification of fetal fraction in a limited amount of blood sample.

Such method can also be used to screen a rare genetic disease panel (i.e., disease having a high incidence of finite mutations, such as in Ashkenazi Jews, African Americans, Finnish, and Amish groups) using a panel of fetal variations that is clinically relevant at the prenatal stage (e.g., genes associated with PROM, preterm birth, surfactants and congenital diseases).

Example 5

Quantifying the Fraction of Fetal DNA in Maternal Blood Using Multiplex Amplification A peripheral blood sample is obtained from a pregnant female. The blood sample is separated into plasma and blood cell components using separation techniques well known in the art.

Multiplex amplification is performed on the plasma using a panel of primer sets (forward and reverse) specific for common polymorphisms. Assuming approximately 80-95% of the sequence counts for one allele are contributed by the mother, the various loci where the mother is homozygous can be determined using a precise counting technique, such as sequencing the amplicons, as described herein. Alternatively, digital PCR can be used to count the loci where the mother is homozygous. The number of alleles different from that of the mother at the same loci are also counted using sequencing or digital PCR methods.

The fetal DNA fraction in maternal blood is calculated using the following equation for each amplicon set:

Fetal fraction=2*(other allele count on locus where mother is homozygous)/(maternal homozygous allele count+other allele count on locus where mother is homozygous). The results for each amplicon are combined to yield the fetal DNA fraction, based on a consensus of the counts from the different sites.

Example 6

Quantifying the Fraction of Fetal DNA in Maternal Blood by Sequencing

A peripheral blood sample is obtained from a pregnant female. The blood sample is separated into plasma and blood cell components using separation techniques well known in the art.

A SNP array (e.g. Illumina BeadArray for SNP calling) is used on the maternal blood cell component to call numerous (e.g. >1000) loci where the mother is homozygous. Sequencing is then used count every loci where the mother is homozygous and to quantify the alleles other than that of the mother at the same loci. The fetal DNA fraction in maternal blood is calculated using the following equation:

Fetal fraction=2*(other allele count on locus where mother is homozygous)/(maternal homozygous allele count+other allele count on locus where mother is homozygous). The results for each loci are combined to yield the fetal DNA fraction, based on a consensus of the counts from the different sites.

Example 7

Quantifying the Fraction of Fetal DNA in Maternal Blood Using Enrichment Methods A peripheral blood sample is obtained from a pregnant female. The blood sample is separated into plasma and blood cell components using separation techniques well known in the art.

An enrichment procedure (e.g. Roche Nimblegen or Raindance RDT 1000 exome enrichment) is used to refine a sub-fraction of the genome: Sequencing, digital PCR or a SNP array can be used on the maternal blood cell component to call positions where the mother is homozygous. Sequencing is then used count every loci where the mother is homozygous and to quantify the alleles other than that of the mother at the same loci. The fetal DNA fraction in maternal blood is calculated using the following equation:

Fetal fraction=2*(other allele count on locus where mother is homozygous)/(maternal homozygous allele count+other allele count on locus where mother is homozygous). The results for each loci are combined to yield the fetal DNA fraction, based on a consensus of the counts from the different sites.

What is claimed is:

1. A method of simultaneously screening for multiple genotypes and/or mutations for a plurality of target sequences in a limited amount of a biological sample from a pregnant female, wherein said sample comprises a mixture of DNA from both the pregnant female and the fetus, the method comprising the steps of:
   a) performing a carrier screen on DNA from the pregnant female and DNA from the fetus's father, to determine a set of single nucleotide polymorphisms (SNPs) that are homozygous and different in the DNA of the pregnant female and in the DNA of the fetus's father;
   b) performing multiplex polymerase chain reaction (PCR) to amplify in the mixture of DNA in the biological sample from the pregnant female the target sequences to be assessed for SNPs in the DNA of the fetus;
   c) sequencing the amplified target sequences in the mixture of DNA;
   d) digitally counting the number of SNPs identified in the amplified sample; and
   e) conducting an analysis that compares the ratios of SNPs identified in the amplified sample to the set of SNPs of the pregnant female and to the set of SNPs of the fetus's father, to determine the genotype inherited by the fetus.

2. The method of claim 1, wherein the biological sample is blood, a blood fraction, saliva, sputum, urine, semen, transvaginal fluid, cerebrospinal fluid, stool, a cell or a tissue biopsy.

3. The method of claim 2, wherein the biological sample is blood.

4. The method of claim 3, wherein the blood is peripheral blood derived from a pregnant woman, or a fraction thereof.

5. The method of claim 1, wherein the sequencing step is performed using sequencing-by-synthesis technology.

6. The method of claim 5, wherein the sequencing step is performed using single molecule sequencing technology.

7. The method of claim 5, wherein the sequencing step is performed using massively parallel sequencing technology.

* * * * *

```
                        SEQUENCE LISTING

<160> NUMBER OF SEQ ID NOS: 10

<210> SEQ ID NO 1
<211> LENGTH: 24
<212> TYPE: DNA
<213> ORGANISM: Artificial Sequence
<220> FEATURE:
<223> OTHER INFORMATION: Synthetic Primer

<400> SEQUENCE: 1
gggagctggt acagaaatga cttc                                              24

<210> SEQ ID NO 2
<211> LENGTH: 22
<212> TYPE: DNA
<213> ORGANISM: Artificial Sequence
<220> FEATURE:
<223> OTHER INFORMATION: Synthetic Probe
<220> FEATURE:
<221> NAME/KEY: misc_feature
<222> LOCATION: (1)..(1)
<223> OTHER INFORMATION: Adenine at position 1 includes a 5' FAM
      fluorescent tag
<220> FEATURE:
<221> NAME/KEY: misc_feature
<222> LOCATION: (22)..(22)
<223> OTHER INFORMATION: Guanine at position 22 includes a 3' TAMRA
      fluorescent tag
```

```
<400> SEQUENCE: 2
agccatcctt cccgggccta gg                                           22

<210> SEQ ID NO 3
<211> LENGTH: 21
<212> TYPE: DNA
<213> ORGANISM: Artificial Sequence
<220> FEATURE:
<223> OTHER INFORMATION: Synthetic Primer

<400> SEQUENCE: 3
ccccacacac atgcacttac c                                            21

<210> SEQ ID NO 4
<211> LENGTH: 21
<212> TYPE: DNA
<213> ORGANISM: Artificial Sequence
<220> FEATURE:
<223> OTHER INFORMATION: Synthetic Primer

<400> SEQUENCE: 4
cctactccca gggctttgat t                                            21

<210> SEQ ID NO 5
<211> LENGTH: 26
<212> TYPE: DNA
<213> ORGANISM: Artificial Sequence
<220> FEATURE:
<223> OTHER INFORMATION: Synthetic Probe
<220> FEATURE:
<221> NAME/KEY: misc_feature
<222> LOCATION: (1)..(1)
<223> OTHER INFORMATION: Anenine at position 1 includes a 5' VIC
      fluorescent tag
<220> FEATURE:
<221> NAME/KEY: misc_feature
<222> LOCATION: (26)..(26)
<223> OTHER INFORMATION: Cytosine at position 26 includes 3' TAMRA
      fluorescent tag

<400> SEQUENCE: 5
aaagagctag gaacaggcaa cttggc                                       26

<210> SEQ ID NO 6

<400> SEQUENCE: 6

000

<210> SEQ ID NO 7

<400> SEQUENCE: 7

000

<210> SEQ ID NO 8

<400> SEQUENCE: 8

000

<210> SEQ ID NO 9

<400> SEQUENCE: 9

000
```

```
<210> SEQ ID NO 10
<211> LENGTH: 19
<212> TYPE: DNA
<213> ORGANISM: Artificial Sequence
<220> FEATURE:
<223> OTHER INFORMATION: Synthetic Primer

<400> SEQUENCE: 10
ttgctcattg cgctgacaa                                                    19
```